United States Patent [19]

Klotman et al.

[11] Patent Number: 5,543,509
[45] Date of Patent: Aug. 6, 1996

[54] METHOD FOR QUANTIFYING LAMININ AND β-ACTIN MESSENGER RNA

[75] Inventors: Paul E. Klotman, Chevy Chase; Leslie A. Bruggeman, Bethesda, both of Md.; Satoshi Horikoshi, Tokyo, Japan

[73] Assignee: The United States of America as represented by the Department of Health and Human Services, Washington, D.C.

[21] Appl. No.: 929,204

[22] Filed: Aug. 14, 1992

[51] Int. Cl.⁶ .......................... C07H 21/02; C07H 21/04
[52] U.S. Cl. ........................ 536/24.33; 536/23.1
[58] Field of Search ...................... 435/320.1; 536/24.3, 536/24.33, 23.1

[56] References Cited

PUBLICATIONS

Kallunki et al, J. Biol. Chem 266:221–228 (1991).
Kleinman et al, Develop. Biol. 122:373–378 (1987).

Primary Examiner—Stephanie W. Zitomer
Assistant Examiner—Eggerton Campbell
Attorney, Agent, or Firm—Foley & Lardner

[57] ABSTRACT

A method for the quantifying of human and murine laminin mRNA transcripts of the A, B1 and B2 chains, and of human and murine β-actin mRNA, entails utilizing particular types of PCR primers and control cRNA.

7 Claims, 5 Drawing Sheets

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

AAGTGGCACA CGGTCAAGAC                                           20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GACAAGAGCT GCATATCCGC                                           20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

ATACTTCGCC TATGACTGTG                                            20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CACATGCAGT GTCCGTGAAC                                            20

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GAGGAATACT GTGTGCAGAC  20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

TCTCGCAGGA ACCACTGTAG  20

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GCCCAGAGCA AGAGAGGTAT  20

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GGCCATCTCT TGCTCGAAGT  20

( 2 ) INFORMATION FOR SEQ ID NO:9:

( i ) SEQUENCE CHARACTERISTICS:
        ( A ) LENGTH: 222 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GAGGAATGTG CAGACATACT TCGCCTATGA CTGTGGCCCA GAGCAAGAGA GGCATAAGTG  60

GCACACGGTC AAGACGAATA CAAGCTTGGG CTGCAGGTCG ACTCTAGAGG ATCCCCGGGC  120

GAGCTCGAAT TCCGGTCTCC CCTACAGTGG TTCCTGCGAG AGTTCACGGA CACTGCATGT  180

GACTTCTGAG CAAGAGATGG CCGCGGATAT GCAGCTCTTG TC  222

METHOD FOR QUANTIFYING LAMININ AND β-ACTIN MESSENGER RNA

BACKGROUND OF THE INVENTION

The present invention relates generally to the quantitation of human and murine laminin mRNA, as well as human and murine β-actin mRNA.

The polymerase chain reaction (PCR) makes possible the amplification of specific segments of nucleic acids via in vitro enzymatic synthesis and is thus a powerful tool for the detection of particular gene transcripts where standard methods may be limited by the small amount of starting tissue available or by the low abundance of transcripts. In the PCR technique, short oligonucleotide primers are synthesized to match opposite ends of the nucleic acid sequence to be amplified. The target sequence flanked by the primers need not be known. In the first PCR cycle, a sample of DNA or RNA (converted to cDNA prior to use in the PCR technique) is extracted from a specimen, denatured, and hybridized with the primers, which are present in molar excess. A polymerase catalyzes the duplication of the target sequence by the addition of deoxynucleotide triphosphates (dNTPs) to the primers at their 3' ends. The dNTPs attached to the primers complement the nucleic acid sequence of the target and thus duplicate the sequence of one strand of the original DNA.

In the second step of the cycle, the replicated DNA is denatured, hybridized with the oligonucleotide primers, and returned to polymerization conditions to again duplicate the target sequence. This sequence is then repeated, and the repetitive cycle of primer annealing, primer extension, and denaturation of the template/PCR product results in rapid, exponential, and voluminous amplification of specific segments of DNA or RNA. Thus, the PCR process is useful for detection of small amounts of nucleic acid or for acquiring sufficient quantities of DNA or RNA for research. See U.S. Pat. Nos. 4,683,195 and 4,800,159, the respective contents of which are incorporated herein by reference.

Compared with other detection methods, such as northern blot analysis, PCR provides a more sensitive and accurate method for detecting the presence of relatively small quantities of DNA or RNA. PCR has also been used to quantify small quantities of mRNA. Thus, Wang et al., *Proc. Nat'l Acad. Sci.* (U.S.A.) 86: 9717–21 (1989), disclose using PCR and a DNA control template to quantify lymphokine mRNA from samples as small as 1 ng. Laminin is an extracellular matrix glycoprotein consisting of three polypeptide chains, A, B1 and B2, each coded for by a separate gene. In contrast, β-actin is an intracellular protein and consists of only one polypeptide chain. Also, the β-actin gene is regulated differently than are the laminin genes.

The expression of laminin is of extreme interest due to the role of laminin in diverse biological activities such as the induction of cellular adhesion, differentiation, migration, and growth of many cell types. For example, laminin is involved in the development of normal kidney and its disregulation contributes to glomerulosclerosis in renal disease.

Lack of sufficient biopsy material containing laminin and β-actin genes combined with low transcription level of these genes have hindered the study of the expression of these genes. As noted above, PCR provides a potential avenue for detecting and quantifying the expression of genes at the transcriptional level. Using PCR to monitor expression of the laminin and β-actin genes, however, poses a difficult task at best. For example, the researcher must use the appropriate primers and reaction parameters because it is known that certain reaction parameters that function efficiently for amplification with one set of primers may not do so for another set. Moreover, primers may cross hybridize to non-target sequences. In addition, quantitating the amount of amplification which occurs during one complete PCR reaction is difficult due to different efficiencies in annealing rates of different primers and non-linear amplification of target sequences and control sequences.

SUMMARY OF THE INVENTION

The present invention provides a method for the quantifying human and murine laminin mRNA transcripts of the A, B1, and B2 chains and human and murine β-actin mRNA which comprises utilizing particular PCR primers and control cRNA. The present invention also provides a DNA control template and primers used to quantify the human and murine laminin mRNA transcripts.

It is an object of the present invention, therefore, to quantify human and murine laminin mRNA transcripts of A, B1 and B2 chains and human and murine β-actin mRNA.

It is a further object of the invention to provide primer pairs for quantifying human and murine laminin mRNA transcripts of the A, B1 and B2 chains and human and murine β-actin mRNA.

It is yet a further object of the invention to provide a DNA control template that is transcribed to produce a cRNA transcript that acts as a control for quantifying human and murine laminin mRNA transcripts of the A, B1 and B2 chains and human and murine β-actin mRNA.

In accomplishing these and other objects, there has been provided, in accordance with one aspect of the present invention, a method for determining the amount of laminin mRNA transcripts in a sample where said laminin mRNA transcripts are selected from the group consisting of mRNA transcripts, respectively, for the laminin A chain, the laminin B1 chain and laminin B2 chain. The inventive method comprises (a) adding a known amount of control cRNA to a reaction mixture containing cellular mRNA; (b) reverse transcribing the control cRNA and the cellular mRNA in the reaction mixture to obtain control cDNA and laminin target cDNA; (c) coamplifying the laminin control cDNA and the laminin target cDNA by the polymerase chain reaction to obtain amplified laminin control cDNA and amplified laminin target cDNA, the polymerase chain reaction using one pair of primers selected from the group consisting of laminin A, laminin B1, or laminin B2 primer pairs; (d) subjecting the amplified laminin control cDNA and laminin target cDNA to electrophoresis; (e) measuring the amount of the laminin target cDNA and the laminin control cDNA present in the electrophoretic gel; and (f) determining the amount of the laminin mRNA transcripts in the sample by extrapolating against a standard curve generated for laminin control cRNA. In preferred embodiments, the mRNA transcripts are either laminin A transcripts, laminin B1 transcripts or laminin B2 transcripts and the primer pair is either a laminin A primer pair, a laminin B1 primer pair or a laminin B2 primer pair, respectively.

In accordance with another aspect of the present invention, a method has been for determining the amount of β-actin mRNA in a sample, which method comprises (a) adding a known amount of control cRNA to a reaction mixture containing cellular mRNA; (b) reverse transcribing the control cRNA and the cellular mRNA in the reaction mixture to obtain control cDNA and β-actin target cDNA; (c) coamplifying the β-actin control cDNA and the β-actin target cDNA by the polymerase chain reaction to obtain amplified β-actin control cDNA and amplified β-actin target cDNA, the polymerase chain reaction using a β-actin primer pair; (d) subjecting the amplified β-actin control cDNA and β-actin target cDNA to electrophoresis; (e) measuring the amount of the β-actin target cDNA and the β-actin control cDNA present in the electrophoretic gel; and (f) determining the amount of the β-actin mRNA transcripts in the sample by extrapolating against a standard curve generated for β-actin control cRNA.

BRIEF DESCRIPTION OF DRAWINGS

FIG. 1 (SEQ ID NO:9) shows the arrangement and nucleotide sequence of a DNA control template designated pSH4, used for the quantitation of human and murine laminin and β-actin genes. In particular.

DETAILED DESCRIPTION OF THE INVENTION

Figures 1A, 1B:
FIG. 1A depicts a 222 base pair DNA fragment containing a symmetric arrangement of the 5' and 3' primers used for the amplification of the three laminin mRNA transcript chains, A, B1 and B2, and β-actin mRNA.
FIG. 1B depicts the nucleotide sequence of the DNA control template, pSH4, and the restriction sites located within the polylinker.

A method has been discovered for quantifying laminin mRNA transcripts and β-actin mRNA wherein a known quantity of RNA complementary to control template DNA ("control complementary RNA" or "cRNA") and cellular mRNA isolated from cells suspected of expressing laminin and/or β-actin are placed in the same reaction mixture. The control cRNA and cellular mRNA are then reverse transcribed to produce amplified control cDNA and amplified laminin and/or β-actin cDNA, depending upon which primer pair(s) were used to amplify the RNA in the reaction mixture and what types of mRNA were present in the reaction mixture.

For example, if a primer pair was used that is capable of hybridizing only to β-actin nucleotide sequences and β-actin mRNA was present in the reaction mixture, then only β-actin cDNA would be amplified. Similarly, if a primer pair was used that is capable of hybridizing only to laminin A chain nucleotide sequences, then only laminin A chain cDNA would be amplified provided laminin A chain mRNA was present in the reaction mixture.

The amplification reaction is terminated in the exponential phase and the amplification products are then subjected to electrophoresis followed by autoradiography or any other suitable means for determining the amount of amplification. The amount of laminin and/or β-actin mRNA can then be determined by extrapolating against a standard curve generated for the control cRNA of each type of mRNA, i.e., laminin A chain, laminin B1 chain, laminin B2 chain and β-actin mRNA.

The standard curve can be generated by plotting the band intensity or CPM versus concentration of added control cRNA. Thus, for each sample of RNA from human biopsy material, individual curves are generated using at least three different concentrations of control cRNA. The results should be the same with each control cRNA concentration, assuming amplification is in the linear range. This will ensure that template interference does not occur at the concentrations of templates and unknown RNA in each tube. See Wang et al., Proc. Nat'l Acad. Sci. (U.S.A.) 86: 9717–21 (1989), the contents of which are hereby incorporated by reference.

Table 1 lists the 5' and 3' primers useful in the polymerase chain reaction to amplify the cDNA sequences corresponding to both human and mouse laminin A, B1, and B2 genes and the β-actin genes. The term "primer pair" is used in this description to denote a set of 5' and 3' primers specific to a particular mRNA species. Thus, the 5' and 3' primers which are specific to Laminin A are referred to as a "laminin A primer pair." Generally, a given primer must be long enough to form a stable complex with the template molecule under the chosen PCR conditions.

TABLE 1

Primers for Amplification of Mouse and Human Target mRNA

| mRNA (SEQ ID NOS 1-8, respectively) species | | 5' primers | 3' primers | Size of PCR product (bp) mRNA | Control |
|---|---|---|---|---|---|
| Laminin | A | 5'-AAGTGGCACACGGTCAAGAC-3' | 5'-GACAAGAGCTGCATATCCGC-3' | 327 | 166 |
| | B1 | 5'-ATACTTCGCCTATGACTGTG-3' | 5'-CACATGCAGTGTCCGTGAAC-3' | 408 | 166 |
| | B2 | 5'-GAGGAATACTGTGTGCAGAC-3' | 5'-TCTCGCAGGAACCACTGTAG-3' | 331 | 166 |
| | β-actin | 5'-GCCCAGAGCAAGAGAGGTAT-3' | 5'-GGCCATCTCTTGCTCGAAGT-3' | 513 | 166 |

Underlined nucleotides indicate divergence between human and mouse sequences. Human sequences are given.

The primer pairs were selected to maximize common nucleotide sequences between human and mouse for the three laminin chains, A, B1, and B2 and β-actin. The region amplified by each set of primer pairs are as follows (nucleotide numbers are according to the original reference): laminin A: nucleotides 1201–1527, Olsen et al., *Lab. Invest.* 60: 772–82 (1989); laminin B1: nucleotides 430–837, Pikkarainen et al., *J. Biol. Chem.*, 262: 10454–62 (1987); laminin B2: nucleotides 121–451, Pikkarainen et al., *J. Biol. Chem.* 263: 6751–58 (1988); and β-actin: nucleotides 172–684, Ponte et al., *Nucl. Acid Res.* 12: 1687–96 (1984). The respective contents of which are incorporated herein by reference. Each amplified product contains a unique restriction site so that a specific digestion pattern can be used in place of sequencing to confirm the accuracy of the amplified sequences.

The primers also provide a means for constructing the DNA control template.

FIG. 1A presents the arrangement of the DNA control template, and FIG. 1B details the nucleotide sequence that makes up the DNA control template.

The control cRNA of the subject invention is complementary to the DNA control template, pSH4, as depicted in FIG. 1B. The control cRNA may be produced by using the pSH4 as a template or it can be produced by nucleotide synthesis using standard well known procedures.

Accordingly, the control cRNA contains nucleotide sequences corresponding to the laminin A, laminin B1, and laminin B2 chains as well as nucleotide sequences corresponding to the β-actin protein. Thus, the target cDNA coding for the laminin chains and β-actin and control cDNA utilize the same primers. As a result, there is no difference in primer efficiency between the amplification of the target and control cDNA's. Thus, provided amplification of the control cDNA and target cDNA is stopped during the exponential phase of amplification, an accurate measurement of the amount of target mRNA can be determined by comparing the amount of target cDNA to the amount of control cDNA.

EXAMPLE 1

Amplification and Detection of Target and Control cDNA

1. Synthesis of Oligonucleotide Primers

Oligonucleotides were synthesized using the 380B DNA synthesizer (Applied Biosystems, Foster City, Calif.).

2. Construction of DNA Control Template

The DNA control template depicted in FIG. 1 was constructed using an oligonucleotide overlap extension technique and amplification by PCR. The synthesized DNA control template was subcloned into the ClaI site of pBlueScript KS(±) (Stratagene, La Jolla, Calif.) and designated pSH4. This plasmid has T7/T3 promoters immediately flanking the cloning polylinker such that complementary RNA (cRNA) to either strand can be generated from the DNA control template.

3. Synthesis of Control cRNA

Control cRNA was generated by linearization of pSH4 with ScaI digestion followed by transcription with T7 RNA polymerase (Boehringer Mannheim, Indianapolis, Ind.). The cRNA was digested with DNase I (RNase free) to remove template DNA from the cRNA preparation.

4. Preparation of Cellular RNA From Murine Kidneys

Kidneys from new born and three-week-old mice were harvested following euthanasia, immediately frozen in liquid nitrogen, and total cellular RNA was prepared using the method described by Chirgwin et al., *Biochem.*, 18:5294–5300, 1979. The final RNA pellets were resuspended in 50 µl of diethylpyrocarbonate-treated (DEPC) water.

5. Amplification of Target cDNA and DNA Control Template

Total cellular RNA from kidneys was converted to cDNA using reverse transcriptase (RT). The RT mixture contained: 0.5 µg of total cellular RNA, 500 µM dNTPs, 10 units of RNAsin (Promega, Madison, Wis.), 50 pmol of random hexamer (Boehringer Mannheim Corp., Indianapolis, Ind.), 25 units of avian myeloblast virus (AMV) reverse transcriptase (Boehringer Mannheim), 50 mM Tris-HCl (pH 8.0), 50 mM KCl, 5 mM $MgCl_2$, 5 mM DTT, and 500 ng bovine serum albumin in a total volume of 10 µl. The RT mixture was incubated at 42° C. for 40 min, heated at 95° C. for 10 min, and then slowly cooled to 24° C.

PCR amplification was performed immediately following the RT reaction by adding 5 µl of 10× PCR buffer (100 mM Tris-HCl pH 8.3, 500 mM KCl, 15 mM $MgCl_2$, 0.01% gelatin), 30 ng of the DNA control template, 500 nM of each 5' and 3' primer, 100 nCi [α-$^{32}$P]dCTP and 1 unit of Taq polymerase (Boehringer Mannheim), to a total volume of 50 µl water. The PCR mixture was overlaid with mineral oil and then amplified in a thermal cycler (Coy Laboratory Products, Ann Arbor, Mich.) for 25 cycles. The amplification profile was as follows: denaturation at 94° C. for 1 min, primer annealing at 55° C. for 1 min, and extension of 72° C. for 2 min. For laminin B2 chain amplification, the temperature for primer annealing was reduced to 50° C. and the temperature for extension was reduced to 60° C.

6. Detection of Amplified Products

The amplified products of the PCR were analyzed by restriction enzyme digestion followed by polyacrylamide gel electrophoresis. The PCR sample was extracted once with phenol/chloroform/isoamyl alcohol (25:24:1), once with chloroform, and precipitated with 1/10 volume 3M sodium acetate and 2 volumes 95% ethanol. The pellet was resuspended in 50 µl of water and 10 µl aliquots were digested with an appropriate restriction enzyme, analyzed by electrophoresis on 5% polyacrylamide gels, and the dried gels were exposed to X-ray film or to one of two phosphorimage analysis systems: Phosphorimager (Molecular Dynamics, Sunnyvale, Calif.), or Fujix Bio-Imager BAS2000 (Fuji Photofilm, Inc., Tokyo, Japan). The restriction enzymes used were as follows: for laminin A, PvuII; for laminin B1, ScaI; for laminin B2, DraIII; and for β-actin, BgII.

FIGS. 4A–4D demonstrate the digestion patterns of a typical RT/PCR amplification of total cellular mRNA. The amplified products are designated by an asterisk and the amplified products sizes are compiled in Table 1. Amplified products were verified by restriction enzyme digestion marked with arrowheads. Using the laminin A primer pair, a 327 bp fragment of the laminin A chain mRNA was amplified. Digestion by PvuII generated 223 bp and 104 bp fragments. Using the laminin B1 primer pair, a 408 bp fragment of the laminin B1 chain mRNA was amplified and digestion by ScaI generated 279 bp and 129 bp fragments. Using the laminin B2 primer pair, a 331 bp fragment of the laminin B2 chain mRNA was amplified and digestion by DraIII generated 208 bp and 123 bp fragments. Using the β-actin primer pair, a 331 bp fragment of the laminin B2 chain mRNA was amplified and digestion by DraIII generated 208 bp and 123 bp fragments. Using the β-actin primer pair, a 513 bp fragment was amplified and digestion with BgII generated 281 bp and 232 bp fragments. The 166 bp fragment amplified from the DNA control template was also verified for accurate amplification by digestion with EcoRI which generated 94 bp and 72 bp fragments. To insure that contaminating genomic DNA had not been co-purified during the preparation of total cellular RNA, each mRNA was amplified in the absence of reverse transcriptase (FIGS. 4A–4D, "-RT"). In all samples tested, only the DNA control template was amplified, indicating that there was no contamination of RNA samples with genomic DNA.

EXAMPLE II

Amplification Profile of the DNA Control Template and Control cRNA

A 166 base pair fragment was amplified from the DNA control template for all of the primer pairs. During the subcloning of the DNA template into pBlueScript, 5 nucleotides of the 5' primer for laminin B2 chain were lost (between nucleotides 7 and 8 in FIG. 1B). The DNA template was amplified successfully however, by reducing the primer annealing temperature to 50° C. and the extension temperature to 60° C. when using the laminin B2 primer pair.

Figure 2:
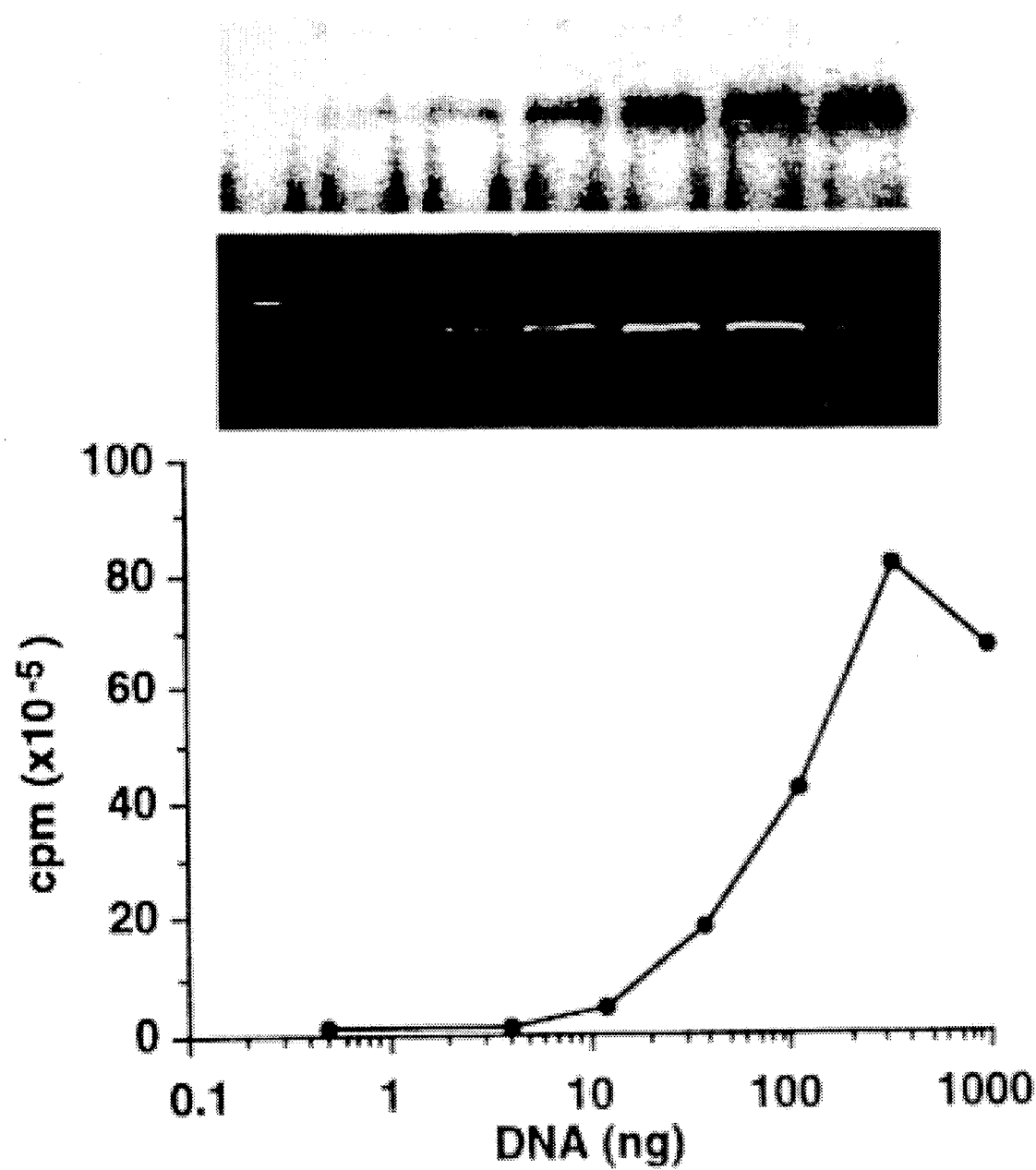
FIG. 2 depicts linearity of amplification of the DNA control template. The DNA control template, undigested plasmid pSH4, was amplified using the β-actin primers to demonstrate a linear response to a range of DNA concentrations. The amplification of the control template is linear in a range of 10 ng to 300 ng. The top panel is an autoradiographic image of the polyacrylamide gel and the lower panel is a photograph of the ethidium bromide staining of the same gel. The graph represents the quantitation of the radiographic image using a phosphorimager (Molecular Dynamics) which calculates the $^{32}P$ disintegrations (cpm) in each band.

As shown in FIG. 2, amplification of the DNA control template (undigested plasmid DNA) was linear in the range of 10 to 300 ng ($3 \times 10^9$ to $8 \times 10^{10}$ molecules). Amplification of increasing amounts of pSH4 using the β-actin primers was shown.

Figure 3:
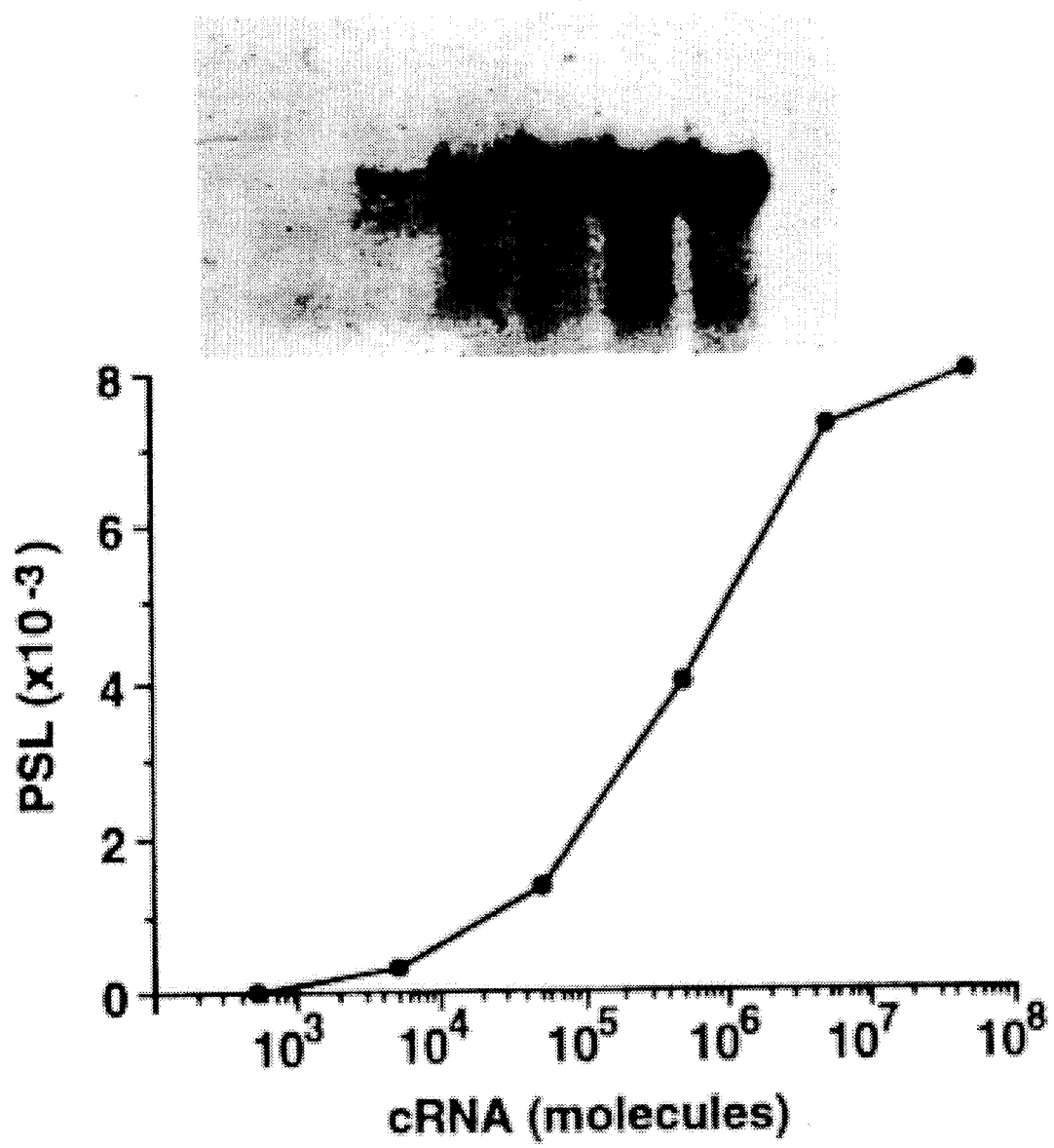
FIG. 3 depicts the linearity of amplification of complementary RNA (cRNA). The cRNA is complementary to the DNA control template. Serial 1:10 dilution of cRNA transcribed from the control template pSH4 was amplified using the laminin A chain primer pair. (Lanes 1 through 5). Lane 6 was the amplification of cRNA without reverse transcription. The graph represents the quantitation of the radioactive bands using radiographic analysis (Fujix), where photostimulated luminescence (PSL) is directly proportional to $^{32}P$ disintegrations. The top panel is an autoradiographic image of the polyacrylamide gel.
Figure 4A:
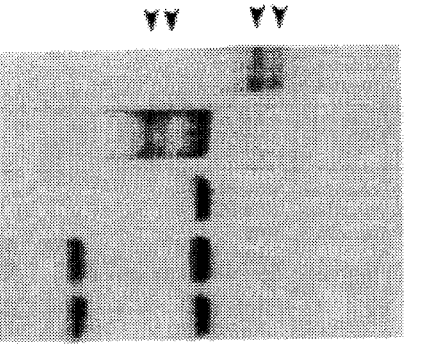
FIGS. 4A–4D depict the amplification of control DNA and total cellular RNA isolated from mouse kidneys. Primer pairs used in each amplification are indicated at the top of each panel. The band at 166 bp represents the amplification of the DNA control template. The bands marked by the asterisk represent the amplification of target cDNA, the target cDNA produced by reverse transcription of the target mRNA, and the bands marked by the arrowheads represent the restriction digestion of the amplified cDNAs (NB, new born mouse RNA; 3W, three week-old mouse RNA; NB, RT-, new born mouse RNA amplified without reverse transcription). The final lanes represent restriction digests of amplified cDNAs using the restriction enzymes indicated at the top of each lane.
Figure 4B:
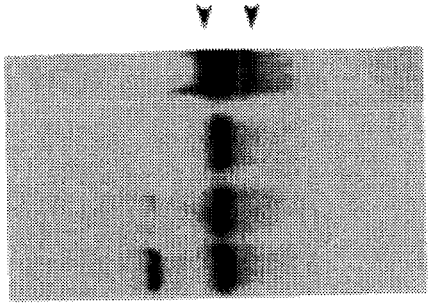
Figure 4C:
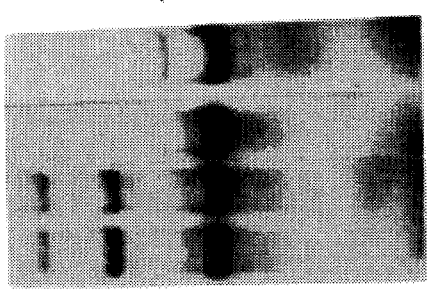
Figure 4D:
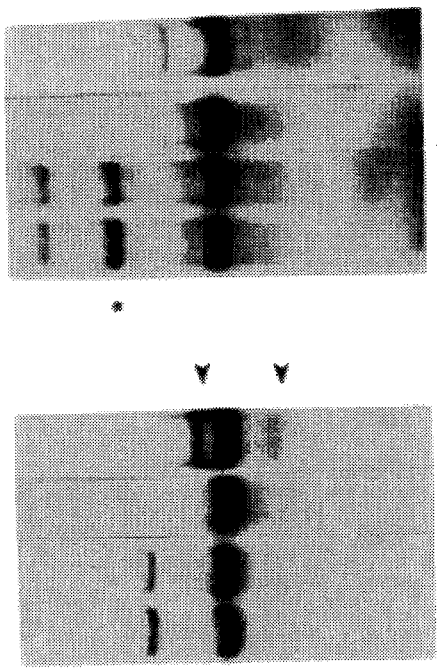
Figure 5:
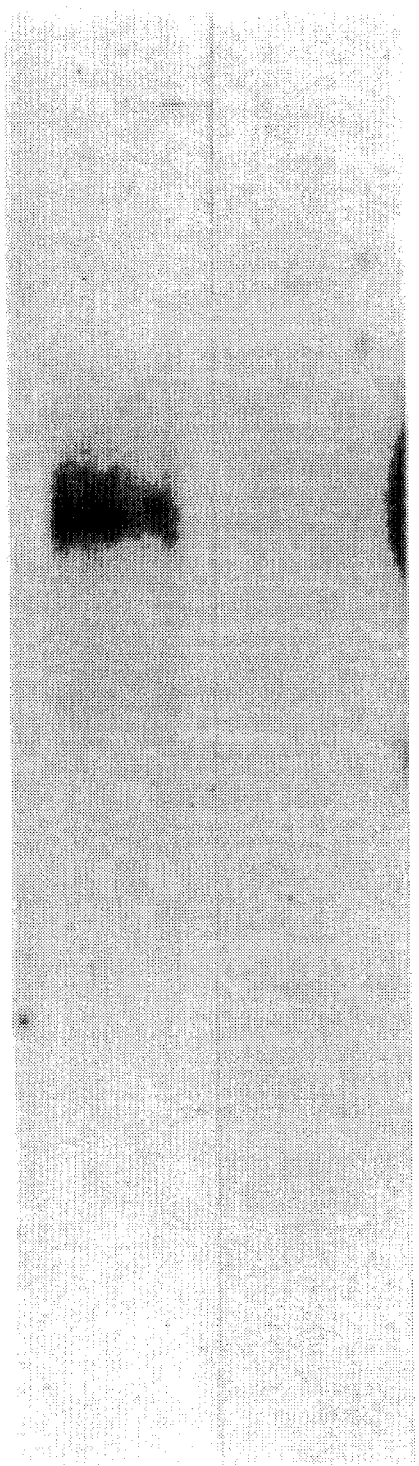
FIG. 5 depicts northern analysis of total cellular RNA isolated from mouse kidneys. Ten micrograms of total cellular RNA were fractionated on a 0.8% agarose/formaldehyde gel, transferred to nitrocellulose and hybridized with a laminin B2 probe. Molecular weight markers are given in kilobase pairs (Kb), and 18s and 28s RNA are marked with arrows (NB, new born mouse; 3 wk, 3 week-old mouse).

As shown in FIG. 3, amplification of the cRNA from pSH4 was also linear in a range from 10 pg to 0.1 pg ($5 \times 10^4$ to $5 \times 10^6$ molecules). Under these conditions, the limit of detection was $5 \times 10^3$ molecules. Both ethidium bromide staining and radiographic images of the polyacrylamide gels of the amplified products were suitable for quantitation by laser densitometry or phosphorimage analysis.

EXAMPLE III

Quantitation of Laminin A mRNA 0.5 µg of total cellular RNA and 0.1 ng of control cRNA in a reverse transcriptase reaction mixture is incubated at 42° C. for 40 min, heated at 95° C. for 10 min, and then slowly cooled to 24° C. to produce target cDNA and control cDNA. The reaction mixture contains 500 µM dNTPs, 10 units of RNAsin, 50 pmol of random hexamer, 25 units of avian myeloblast virus (AMV) reverse transcriptase, 50 mM Tris-HCl (pH 8.0), 50 mM KCl, 5 mM $MgCl_2$, 5 mM DTT, 500 ng bovine serum albumin in a total volume of 10 µl.

The control cRNA is generated by digestion of pSH4 with ScaI, transcription by polymerase T7, digestion with RNase-free DNase I, and precipitation with sodium acetate and ethanol.

The control cRNA and target cDNA is then amplified by PCR by adding to the reaction mixture 5 µl of 10× PCR buffer (100 mM Tris-HCl pH 8.3, 500 mM KCl, 15 mM $MgCl_2$, 0.01% gelatin), 500 nM of laminin A primer pair, 100 nCi [α-$^{32}$P]dCTP and 1 unit of Taq polymerase, to a total volume of 50 µl water. The PCR mixture is overlaid with mineral oil and then amplified in a thermal cycler for 25 cycles. The amplification profile is as follows: denaturation at 94° C. for 1 min, primer annealing at 55° C. for 1 min, and extension at 72° C. for 2 min. The amplified laminin A target cDNA and laminin control cDNA are subject to polyacrylamide gel electrophoresis followed by autoradiography.

The amount of laminin A mRNA in the sample is determined by extrapolating against a standard curve generated for laminin A control cRNA.

EXAMPLE IV

Quantitation of Laminin B2 mRNA 0.5 µg of total cellular RNA and 0.1 ng of control cRNA in a reverse transcriptase reaction mixture is incubated at 42° C. for 40 min, heated at 95° C. for 10 min, and then slowly cooled to 24°20 C. to produce target cDNA and control cDNA. The reaction mixture contains 500 µM dNTPs, 10 units of RNAsin, 50 pmol of random hexamer, 25 units of avian myeloblast virus (AMV) reverse transcriptase, 50 mM Tris-HCl (pH 8.0), 50 mM KCl, 5 mM $MgCl_2$, 5 mM DTT, 500 ng bovine serum albumin in a total volume of 10 µl.

The control cRNA is generated by digestion of pSH4 with ScaI, transcription by polymerase T7, digestion with RNase-free DNase I, and precipitation with sodium acetate and ethanol.

The control cRNA and target cDNA then is PCR-amplified by adding to the reaction mixture 5 µl of 10× PCR buffer (100 mM Tris-HCl pH 8.3, 500 mM KCl, 15 mM $MgCl_2$, 0.01% gelatin), 500 nM of laminin B2 primer pair,100 nCi [α-$^{32}$P]dCTP and 1 unit of Taq polymerase, to a total volume of 50 µl water. The PCR mixture is overlaid with mineral oil and then amplified in a thermal cycler for 25 cycles. The amplification profile is as follows: denaturation at 94° C. for 1 min, primer annealing at 50° C. for 1 min, and extension at 60° C. for 2 min. The amplified laminin B2 target cDNA and laminin control cDNA are subject to polyacrylamide gel electrophoresis followed by autoradiography.

The amount of laminin B2 mRNA in the sample is determined by extrapolating against a standard curve generated for laminin B2 control cRNA.

From the foregoing description, one skilled in the art can easily ascertain the essential characteristics of this invention and, without departing from the spirit and scope thereof, can make various changes and modifications of the invention to adapt it to various usages and conditions.

---

What is claimed is:

1. An isolated and purified plasmid designated pSH4.

2. A DNA control template for determining the amount of laminin mRNA transcripts or β-actin transcripts in a sample, consisting of an isolated and purified DNA sequence depicted in FIG. 1B.

3. A control cRNA template for determining the amount of laminin mRNA transcripts or β-actin transcripts in a sample, consisting of an isolated and purified RNA sequence complementary to the DNA sequence depicted in FIG. 1B.

4. A laminin A primer pair, wherein the 5' primer of said primer pair consists of Seq. ID No. 1 and the 3' primer of said primer pair consists of Seq. ID No. 2.

5. A laminin B1 primer pair, wherein the 5' primer of said primer pair consists of Seq. ID No. 3 and the 3' primer of said primer pair consists of Seq. ID No. 4.

6. A laminin B2 primer pair, wherein the 5' primer of said primer pair consists of Seq. ID No. 5 and the 3' primer of said primer pair consists of Seq. ID No. 6.

7. A laminin B2 primer pair, wherein the 5' primer of said primer pair consists of Seq. ID No. 7 and the 3' primer of said primer pair consists of Seq. ID No. 8.

* * * * *